United States Patent
Levin et al.

(10) Patent No.: US 10,856,798 B2
(45) Date of Patent: Dec. 8, 2020

(54) MONITORING SYSTEM FOR CONTINUOUSLY SENSING THE UTERUS

(71) Applicant: FERTIGO MEDICAL LTD., Zichron Ya'Akov (IL)

(72) Inventors: Victor Levin, Haifa (IL); Tsafrir Kolatt, Zichron Ya'Akov (IL); Adi Strauss, Yokneam Moshava (IL)

(73) Assignee: FERTIGO MEDICAL LTD, Zichron Ya'Akov (IL)

(*) Notice: Subject to any disclaimer, the term of this patent is extended or adjusted under 35 U.S.C. 154(b) by 358 days.

(21) Appl. No.: 15/300,501

(22) PCT Filed: Apr. 1, 2015

(86) PCT No.: PCT/IL2015/050353
§ 371 (c)(1),
(2) Date: Sep. 29, 2016

(87) PCT Pub. No.: WO2015/151102
PCT Pub. Date: Oct. 8, 2015

(65) Prior Publication Data
US 2017/0181687 A1 Jun. 29, 2017

Related U.S. Application Data

(60) Provisional application No. 61/973,284, filed on Apr. 1, 2014, provisional application No. 62/019,445, filed on Jul. 1, 2014.

(51) Int. Cl.
*A61B 5/00* (2006.01)
*A61B 1/04* (2006.01)
(Continued)

(52) U.S. Cl.
CPC ........ *A61B 5/4325* (2013.01); *A61B 1/00071* (2013.01); *A61B 1/043* (2013.01);
(Continued)

(58) Field of Classification Search
CPC ... A61B 5/4325; A61B 1/00071; A61B 1/043; A61B 1/0684; A61B 1/126; A61B 1/303;
(Continued)

(56) References Cited

U.S. PATENT DOCUMENTS 8,128,576 B2* 3/2012 Tracey .................. A61B 5/208
600/135
8,679,014 B2* 3/2014 Bennett .............. A61B 1/00016
600/301

(Continued)

FOREIGN PATENT DOCUMENTS

CN 200939143 Y 8/2007
EP 1562492 B1 1/2007
(Continued)

*Primary Examiner* — Ryan N Henderson
*Assistant Examiner* — Pamela F Wu
(74) *Attorney, Agent, or Firm* — William Dippert; Laurence Greenberg; Werner Stemer

(57) ABSTRACT

A monitoring system comprising: a uterine insert comprising an insert extension, wherein the insert extension comprises at least one sensor; a deployment module engageable with the insert, and configured to allow the insert extension to bend when the module is engaged with the insert; a system control device operationally coupled to continuously receive signals from the at least one sensor and to convert the signals into data representing the signals, and a display operationally coupled to display the data from the system control device.

23 Claims, 15 Drawing Sheets

(51) Int. Cl.
*A61B 1/06* (2006.01)
*A61B 1/307* (2006.01)
*A61B 1/00* (2006.01)
*A61B 1/12* (2006.01)
*A61B 1/303* (2006.01)
*A61B 5/01* (2006.01)
*A61B 5/145* (2006.01)
*A61B 5/1455* (2006.01)

(52) U.S. Cl.
CPC ............ *A61B 1/0684* (2013.01); *A61B 1/126* (2013.01); *A61B 1/303* (2013.01); *A61B 1/307* (2013.01); *A61B 5/0084* (2013.01); *A61B 5/0538* (2013.01); *A61B 5/6875* (2013.01); *A61B 5/01* (2013.01); *A61B 5/14539* (2013.01); *A61B 5/14551* (2013.01); *A61B 2560/04* (2013.01)

(58) Field of Classification Search
CPC ..... A61B 1/307; A61B 5/0084; A61B 5/0538; A61B 5/4836; A61B 5/6875; A61B 5/01; A61B 5/14539; A61B 5/14551; A61B 2560/04; A61B 1/041; A61B 5/43; A61B 5/4306; A61B 5/4318; A61B 5/4331; A61B 5/4337; A61B 5/4343; A61B 5/435; A61B 5/4356; A61B 5/4362; A61B 5/4368; A61B 1/0008; A61B 1/00101; A61B 1/00137; A61B 1/053; A61B 10/0291; A61B 2017/4216; A61B 10/4225
USPC ........ 600/135, 327, 332, 339, 591; 604/515, 604/93.01, 95.01–95.05, 96.01, 264, 288; 128/830, 833, 839; 607/138; 606/193
See application file for complete search history.

(56) References Cited

U.S. PATENT DOCUMENTS

| | | | | |
|---|---|---|---|---|
| 2004/0092825 | A1* | 5/2004 | Madar | A61B 1/041 600/473 |
| 2005/0215858 | A1 | 9/2005 | Vail, III | |
| 2006/0240413 | A1* | 10/2006 | Auttebery | A61B 10/0291 435/5 |
| 2007/0255100 | A1* | 11/2007 | Barlow | A61B 1/0005 600/114 |
| 2008/0108869 | A1 | 5/2008 | Sanders et al. | |
| 2010/0249503 | A1* | 9/2010 | Yazawa | A61B 1/00091 600/109 |
| 2011/0282144 | A1* | 11/2011 | Gettman | A61B 1/041 600/109 |
| 2012/0130272 | A1 | 5/2012 | Layton | |
| 2014/0228715 | A1* | 8/2014 | Schroeder | A61B 5/073 601/2 |
| 2017/0128053 | A1* | 5/2017 | Nakamura | A61B 5/6875 |

FOREIGN PATENT DOCUMENTS

| | | |
|---|---|---|
| JP | S6389137 A | 4/1988 |
| JP | 2004121733 A | 4/2004 |
| JP | 2005211170 A | 8/2005 |
| JP | 2006034346 A | 2/2006 |
| JP | 2010506669 A | 3/2010 |
| RU | 2456031 C1 | 7/2012 |
| RU | 2013114724 A | 8/2013 |
| WO | 2008104888 A2 | 9/2008 |
| WO | 2011038310 A1 | 3/2011 |

\* cited by examiner

MONITORING SYSTEM FOR CONTINUOUSLY SENSING THE UTERUS

CROSS-REFERENCE TO RELATED PATENT APPLICATIONS

This patent application is a U.S. National Phase Application filing under 35 U.S.C. § 371 of PCT Patent Application No. PCT/IL2015/050353, filed Apr. 1, 2015, which in turn is based upon and claims the benefit of the filing dates of U.S. Provisional Patent Application Ser. No. 61/973,284, filed Apr. 1, 2014, and U.S. Provisional Patent Application Ser. No. 62/019,445, filed Jul. 1, 2014, each of which is incorporated herein by reference in its entirety.

FIELD OF THE INVENTION

The present invention relates to a system and a method for monitoring uteri, particularly to help treat infertility.

BACKGROUND OF THE INVENTION

At present the most effective treatments of infertility problems are IVF (In vivo fertilization) methods. In order to prepare a patient's uterus for hosting an embryo during the IVF treatment, the physician may artificially adjust the patient's estrogen hormone levels. The elevated levels control the endometrial prosperity which in turn has a significant effect on the uterus' readiness to receive embryos. In order to prepare a proper environment in the woman and to increase the chances of recovering several healthy and mature eggs, the woman will undergo about two weeks of intensive preparation, including hormonal therapy with "fertility drugs", blood tests and 2-3 scans of ultrasound of the ovaries, as well as biopsies of the endometrium that may be performed before the treatment commences to evaluate the uterus' condition One of the key factors that the physician needs to pay attention to is the patient's reaction to hormones. Measurement of estrogen levels in the blood helps the physician determine how well the uterus is. Furthermore, monitoring of patients receiving HMG (human menopausal gonadotropin) therapy is essential for dosage adjustment and prevention of side effects. Each woman's response to the treatment is different and the administered dose needs to be carefully adjusted.

One of the common side effects of the fertility treatments is fluid retention caused by over-dose of estrogenic hormones given to the patient during the IVF treatment. Some hormones stimulate proliferation and differentiation in the fallopian tube, to increase the tubal mucosal activity. Oestradiol increases the water content of cervical mucus and favors contraction of the uterine endometrium.

In fact, there is a period of 24-48 hours during the weeks of fertility treatment that is optimal for the fertilization, i.e., embryo transfer. This period can be difficult to determine due to all of the factors described above. The determination requires careful and continuous monitoring, which at present entails frequent visits of the patient to a hospital and performance of many labor-intensive tests.

The monitoring can also be used to assess the fluid retention mentioned above, that might be excessive: The occurrence of fluid accumulation within the uterine cavity has been examined in women undergoing IVF-ET to investigate its correlation with tubal disease and effect on the pregnancy outcome. The pregnancy rate was 5.7% in the group of women exhibiting excessive uterine fluid accumulation during IVF-ET cycles. By comparison, a pregnancy rate of 27.1% was achieved in women where no fluid accumulation was detected [http://humrep.oxfordjournals.org/content/17/2/351.full]. Therefore, excessive uterine fluid might well be detrimental to the embryo implantation success rate. Therefore, the detection of excessive retention is important in determining the impact on pregnancy outcome.

The monitoring is performed by either hysteroscopy, ultrasound, which are all single exams performed in the clinics, or by drawn blood samples for which various parameters are assessed. The blood samples, naturally, only reflect systemic properties and are not local/topical of the uterus lining.

In conclusion there is a need for real time monitoring in order to optimize the process of preparation towards fertilization, and in order to reduce side effects. There are no known methods and devices capable of carrying out continuous monitoring over extended periods of time, and optionally also treatments needed for the preparation. An object is to provide a system and a method that overcome the shortcomings of the prior art.

Further objects and advantages of this invention will appear as the description proceeds.

SUMMARY OF THE INVENTION

According to one aspect, a monitoring system is provided, the system comprising:
  a uterine insert comprising an insert extension, wherein the insert extension comprises at least one sensor;
  a deployment module engageable with the insert, and configured to allow the insert extension to bend when the module is engaged with the insert;
  a system control device operationally coupled to continuously receive signals from the at least one sensor and to convert the signals into data representing the signals, and
  a display operationally coupled to display the data from the system control device.

In preferred embodiments the uterine insert further comprises an insert body,
  wherein the insert body comprises flexible engagement means
  and the insert body is couplable to the uterine insert.

The engagement means is for example selected from a group consisting of: curved and notched fins, inflatable elements and combinations thereof.

The insert has a longitudinal axis. In some embodiments the fins point away from the insert extension and at an oblique angle relative to the axis.

In some embodiments the fins are retractable.

In some embodiments the inflatable elements each comprise an asymmetric hole.

In some preferred embodiments the system is configured to allow visual monitoring of uterus tissue.

The monitoring is for example selected from at least one of a group consisting of: glands number and number density, size and distribution; blood vessel density; blood vessel distribution; blood oxygen saturation and total oxygen concentration.

The sensor may be selected from a group consisting of: camera, thermometer, pH sensitive electrode, bioelectrical impedance sensor and combinations thereof.

The insert may comprise a microscope, wherein the microscope comprises the camera.

The system may further comprise an illumination component configured to illuminate for the camera.

In some embodiments the insert further comprises a shutter configured to shut when the insert is disengaged with the module.

In some embodiments the insert further comprises a power supply unit electrically coupled to the at least one sensor.

In some preferred embodiments the insert comprises at least one anti-bacterial composition capable of preventing ascending contamination.

In some preferred embodiments the insert is designed to be positioned in a uterus over an extended period of time.

In some embodiments the insert extension further comprises at least one drawstring that is coupleable to the module, such that when the module is engaged with the insert the module can be employed to draw the at least one drawstring and thereby bend the insert extension.

In some embodiments the system is configured to allow deposition of substances from the insert extension through deposition pores along the insert extension and/or a nozzle at a tip of the insert extension.

In some embodiments the insert extension comprises a primary feeding channel leading throughout the insert extension and to the pores and/or to the nozzle.

In some embodiments the system further comprises a power supply unit electrically coupled to a pump, wherein the pump is coupled to the primary feeding channel.

Some embodiments comprise at least one nozzle configured to allow washing at least one lens of the camera.

In some embodiments the camera is movable by remote control.

The camera is preferably configured to allow a clear view of walls of a uterus.

The insert extension may further comprise a cord, configured to allow performing at least one of the following actions:
  wired communication between the uterine insert and the system control device;
  to help withdraw the insert extension;
  and to help drainage outside a vagina wherein the insert extension is installed.

One or more of the following outputs may be transferrable from the system control device to the uterine insert: image acquisition parameters; electric current; anti-body depositions; fluorophore depositions; hormones depositions; depositions of pharmaceutical compositions, and disinfectant depositions, and one or more of the following inputs are transferrable from the uterine insert to the system control device: still and/or video images; impedance signals; signals reflecting mucosa acidity; signals representing mucosa composition; fluorescence measurement signals; and temperature measurements.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the specification, including definitions, will control. In addition, the materials, methods, and examples are illustrative only and not intended to be limiting.

BRIEF DESCRIPTION OF THE FIGURES

A monitoring system is provided as shown in schematic view in FIG. 1.

DESCRIPTION OF THE PREFERRED EMBODIMENTS

Before explaining at least one embodiment in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

Figure 1:
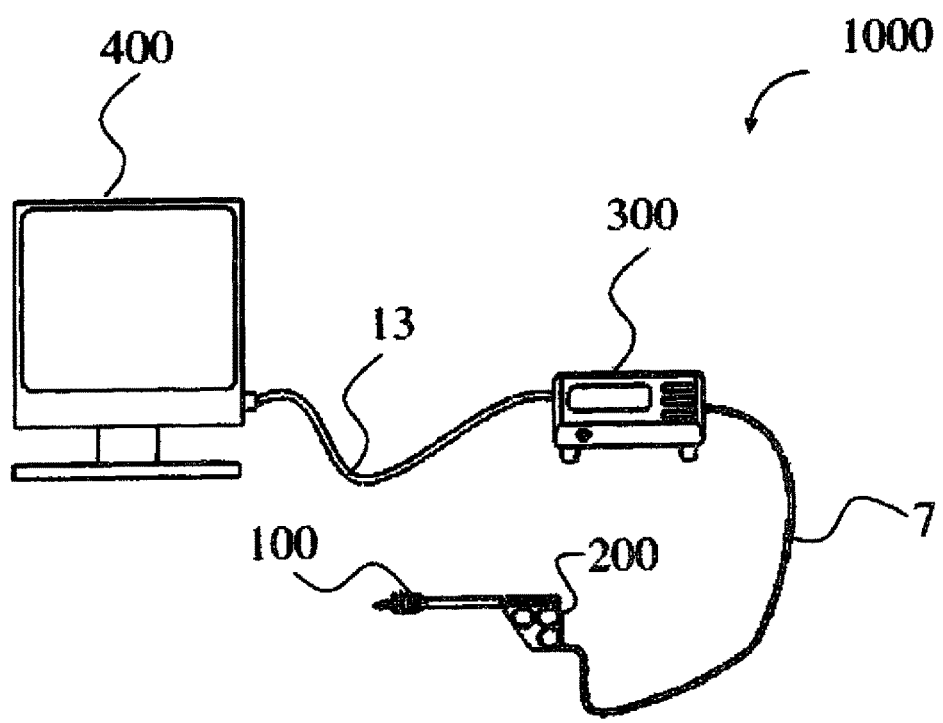

According to one aspect of the invention, a monitoring system is provided. As shown in a schematic view in FIG. 1, the system 1000 comprises a uterine insert 100, a deployment module 200 and a system control device 300. The system 1000 is configured to allow the control device to receive signals that are transmitted from the uterine insert 100. The uterine insert 100 is designed to be positioned in a uterus over an extended period of time.

Figure 2:
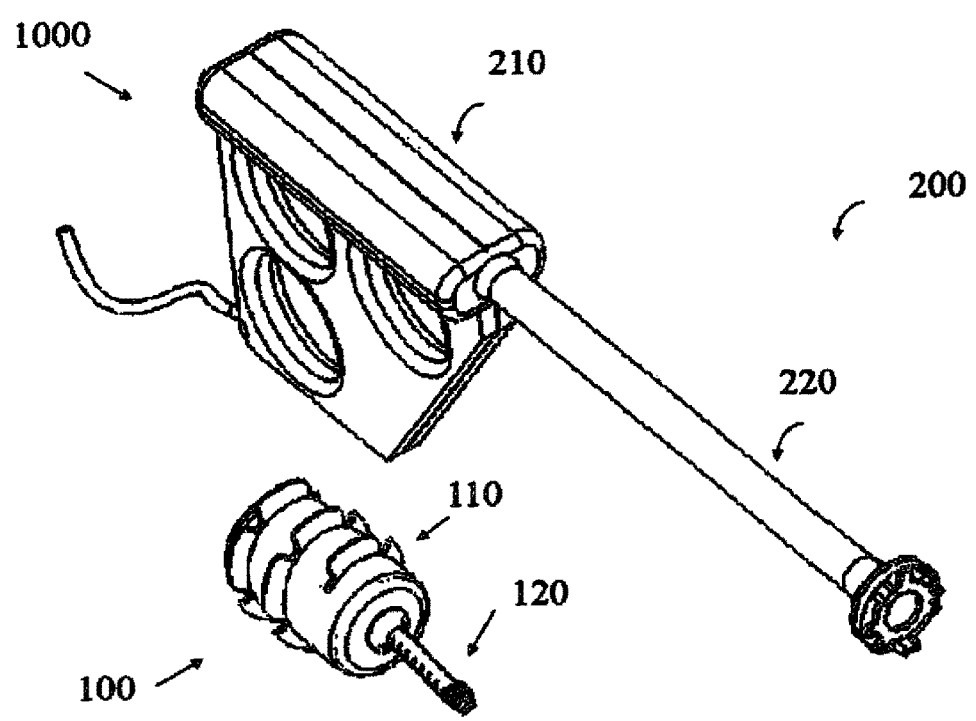
FIG. 2 shows in one perspective view a uterine insert comprising an insert body and an insert extension.
Figure 3:
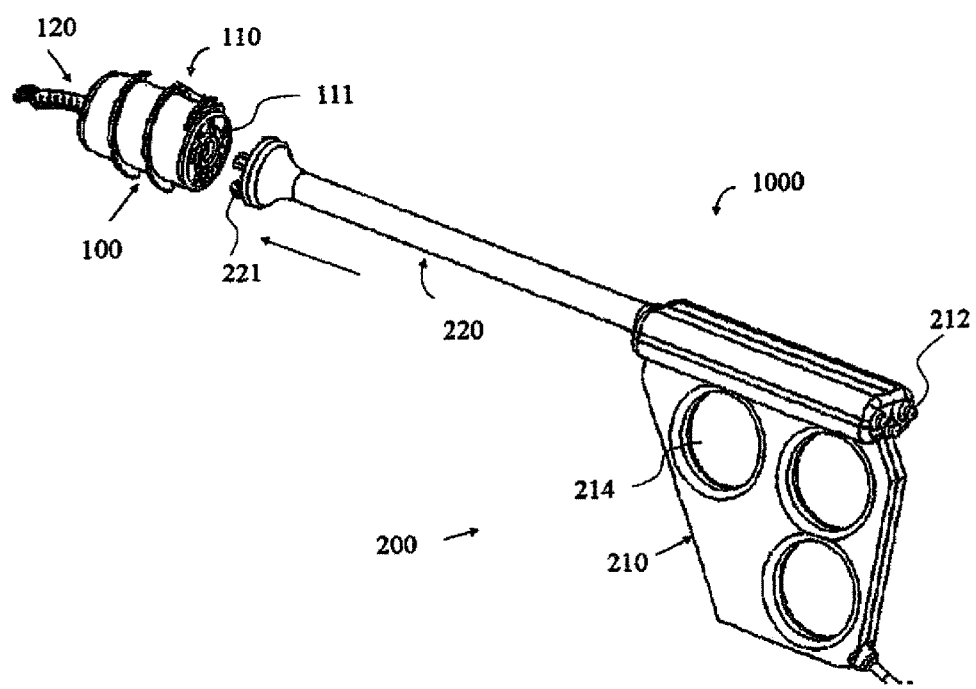
FIG. 3 shows in another perspective view the uterine insert and insert extension shown in FIG. 2.

As shown in FIGS. 2 and 3 in two perspective views, the uterine insert 100 comprises an insert body 110 and an insert extension 120. The module 200 comprises a module body 210 and a module extension 220. The uterine insert 100 and the module 200 are removably engagable with each other; the uterine insert 100 has a socket 111 in the insert body 110 and the module 200 has a plug 221 on the module extension 220 that is engagable with the socket 111. Engagement can be manually performed by careful alignment of the plug 221 and the socket 111 and pushing the uterine insert 100 and the module together. In alternative embodiments the module has a socket and the uterine insert has a plug (not shown), or other means of engagement and disengagement may be employed.

Prior to using the system 1000 the physician typically conducts a standard inspection using ultrasound technology or hysteroscopy of the patient's uterus. The physician may prepare the system 1000 for a first stage of inspection by engaging the uterine insert 100 with the deployment module 200 and testing the system by pumping water into the uterine insert 100 for example, and by other functions.

The module body 210 is essentially a handle that has buttons 212 for manipulation of the uterine insert 100 and finger engagement holes 214 that allow a physician to comfortably grip the module 200. In some embodiments there are no such holes. In some embodiments (not shown) the buttons are touch buttons and/or dials and/or the button shown in the figure, or other known finger-engageable means.

The system comprises an optional locking arrangement (not shown in its entirety) that comprises at least one button 212 on the module 200, which is either mechanically coupled or electrically coupled to the plug 221 or the socket 111, to allow the plug 221 and the socket 111 to be locked to other. In other embodiments there is no locking arrangement.

Figure 4:
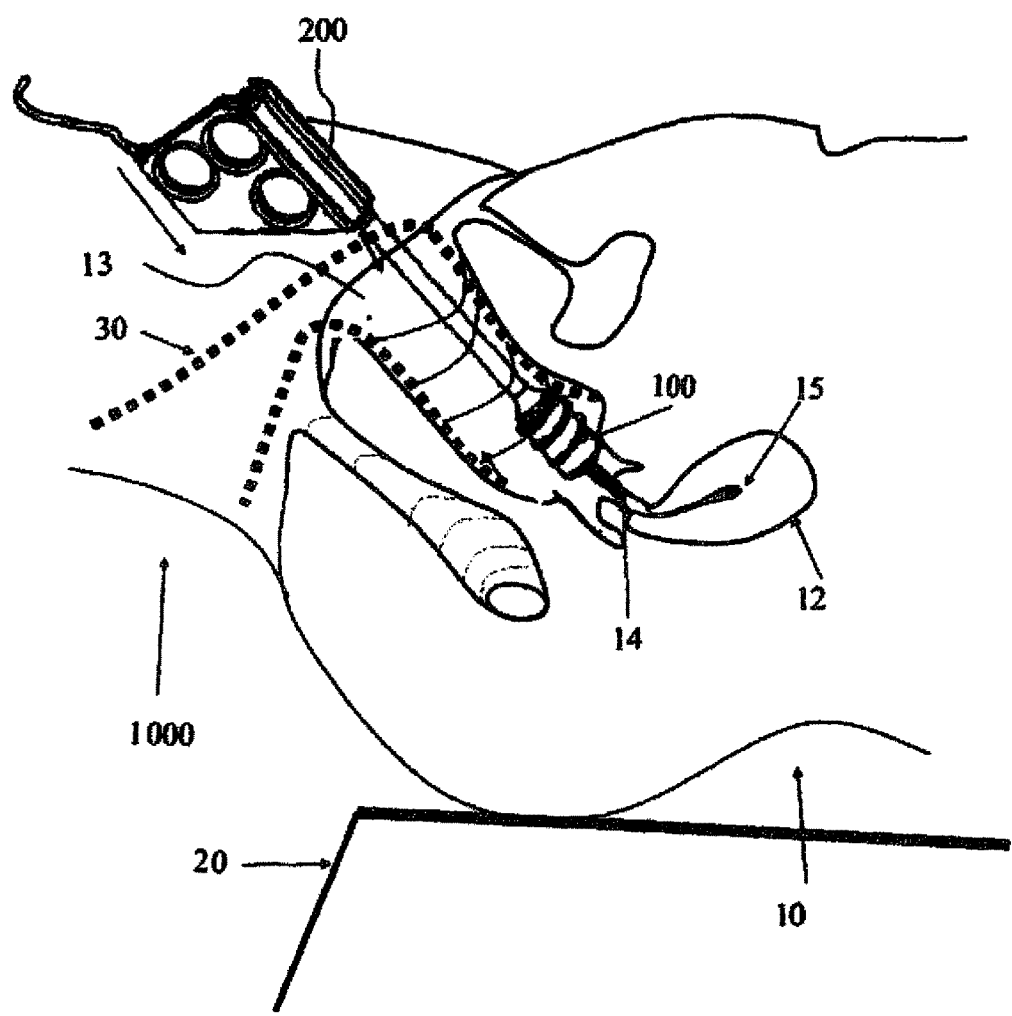
FIG. 4 demonstrates how the system is positioned to monitor and/or treat the reproductive system of a woman.

FIG. 4 demonstrates how the system 1000 is positioned to monitor and/or treat the reproductive system 12 of a woman 10. The woman 10 lies on a suitable treatment bed 20. A speculum 30 is employed to allow the uterine insert 100 access to her reproductive system 12. The uterine insert 100, coupled to the module 200, is introduced into the vagina 13 until reaching cervix entrance 14. At this point the uterine insert extension 120 is bent to allow the extension 120 to travel along the vagina, cervix surface and uterus 15.

Figure 5A:
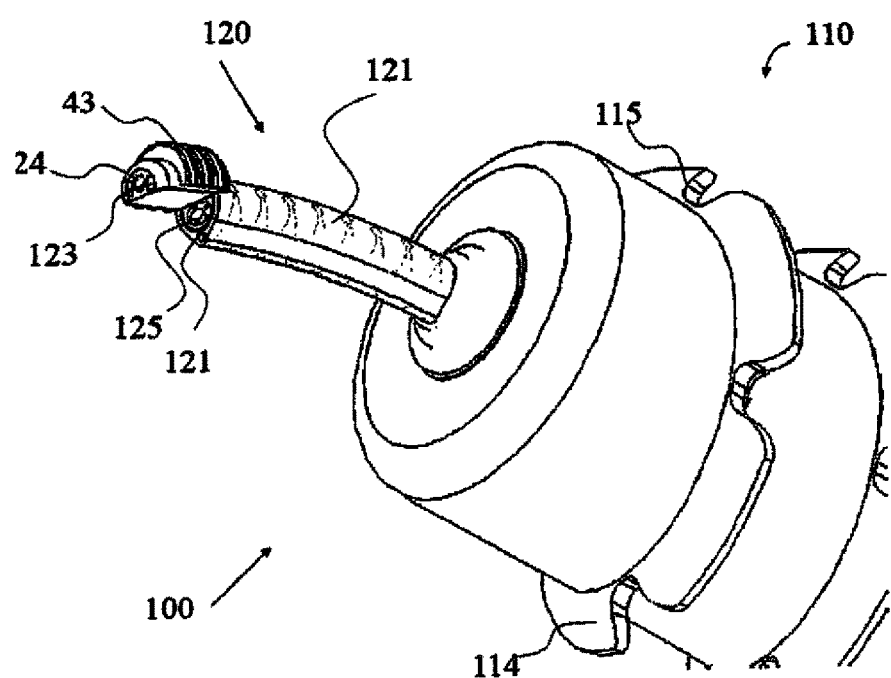
FIG. 5a illustrates in perspective view a section of the uterine insert.

FIG. 5*a* illustrates in perspective view a section of the uterine insert 100. The insert extension 120 comprises a first drawstring 121 that extends along the insert extension 120. One of the buttons of the module (not shown) may be coupled to the first drawstring 121 such as to allow bending the insert extension 120 in the uterus when the module is engaged with the uterine insert 100. In some embodiments pressing the button harder causes the insert extension 120 to increasingly bend and release of the pressure on the button causes the insert extension to increasingly unbend.

Figure 5B:
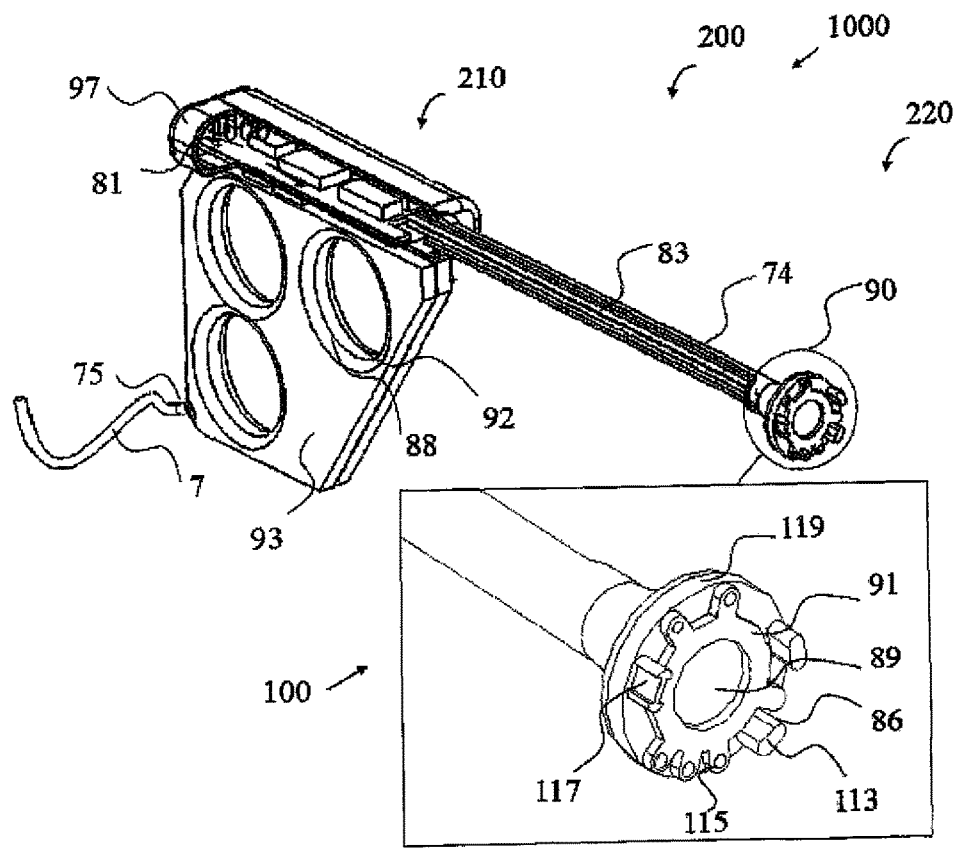
FIG. 5b depicts a module of the system in a frontal perspective sectional view.

FIG. 5*b* depicts the module 200 in a frontal perspective sectional view and Figure Sc shows the same module 200 in a rear perspective sectional view.

The system 1000 provides a feeding cable 7 connected with a strain relief 75 to the module 200. The module body 210 includes: a chassis 97, a feeding cable strain relief 75, control buttons 212, chassis 97, control PCB 81, and handle 93. The chassis 97 is affixed to control PCB 81 by a rigid fixation method (bonding, screws or other means) to the internal side of chassis 97. At the rear side of chassis 97 (as shown in FIG. 4*a*) the control buttons 212 are positioned, they are designed to be protected in the working environment. The bottom of the chassis 97 is ergonomically designed in order to provide support and grip for the physician who has gloved fingers.

The module extension 220 comprises a casing 74, cables 83 and a male docking interface 90. The casing 74 may be shaped as a narrow and long tube, and holds all cables 83 stretched from the module body 210 up to the male docking interface 90. The casing 74 is shaped at a distal end as a funnel to house the docking interface 90. The male docking interface 90 is rigidly connected to casing 74 and the male docking interface 90 is connected to the cables 83 by way of welding the cables to the interface 90, or by another suitable affixing method. The male docking interface 90 includes a structure 119 comprising three docking legs 86 with a face 113, and an alignment notch 117 on each docking leg 86 that has two functions. The first role of the structure 119 is to bridge between the deployment module 200 and the uterine insert 100. The secondary role is to open protecting-fins (not shown here) when the uterine insert 100 is coupled with deployment module 200, or has been disconnected. An electrical finger disk 91, that is shaped allow providing communication and alignment with the female side that is positioned at uterine insert 100, is located on the male docking interface 90 front face. In the middle of the male docking interface 90 there is a clear round area 89, which can be utilized as a position for a guiding camera and illumination. The structure 110 includes a fingers disk 91. In the middle of fingers 95 at the fingers disk 91 there are five electrical connectors 115. The number of connectors 115 is selected according to the functional requirements from the uterine insert 100.

In other embodiments other means of bending/unbending the insert extension are provided.

In some embodiments the bending of the insert extension 120 can be locked and unlocked by a locking mechanism, typically employed by pressing another button on the module.

In some embodiments (not shown) there is a second drawstring extending along the insert extension 120 and the system is configured to allow manipulating the second string by pressing a button on the module body. The manipulation of the second string allows bending the string in a direction essentially perpendicular to the direction of bending of the first string. There is thus an enhanced capability to direct the insert extension.

Once the uterine insert 100 is in a selected location in the uterus, the uterine insert 100 should be left in place for an extended period of time. In some embodiments (not shown) the system further comprises means that allow disengagement of the module from the uterine insert such that no pulling of the uterine insert occurs when disengaging and moving the module apart from the uterine insert, thus helping to avoid undesirable movement of the uterine insert. For example some embodiments may have a locking mechanism for engaging the uterine insert and the module that comprises resilient means which are primed when the uterine insert and module are forced together, and are employed when the locking mechanism is set to disengage the uterine insert from the module. Again, such disengagement could be performed by a button on the module that is coupled to the locking mechanism.

The insert body 110 shown in FIG. 5*a* further comprises soft and flexible curved fins 114 with notches 115 that may help keep the walls of the vagina apart to facilitate insertion of the insert extension 120 into the uterus 15. The notches 115 allow fluid passage between the insert body 110 and the walls. The fins further assist in keeping the insert extension 120 away from the walls of the vagina, as well as immobilize the uterine insert 100. In preferred embodiments the fins 114 are oblique relative to the longitudinal axis A of the uterine insert 100, and preferably point away from the insert extension 120 to best anchor the insert body to the vagina top part, right before the entrance to the cervix. In some embodiments the fins 114 are retractable. The retraction in some embodiments can be performed by retracting means located in the insert body, but controlled by an external control unit (the module or another device), so that the uterine insert can be pulled out without need to connect any device to the uterine insert.

The buttons 212 serve for employing one or more of the following functions, some of which will be further discussed below:

1. Steering;
2. Fins deployment and retraction;
3. Inflating anchoring inflatable components and their deflation before retraction of the uterine insert;
4. Disengagement and engagement of the uterine insert during deployment/retraction, and
5. Substance deposition—disinfectants and/or other substances (water, air, hormones, etc.)

In preferred embodiments the insert extension 120 is coated with an anti-bacterial material capable of preventing ascending contamination. In some preferred embodiments all of the parts of the uterine insert 100 are coated with the material.

Figure 6:
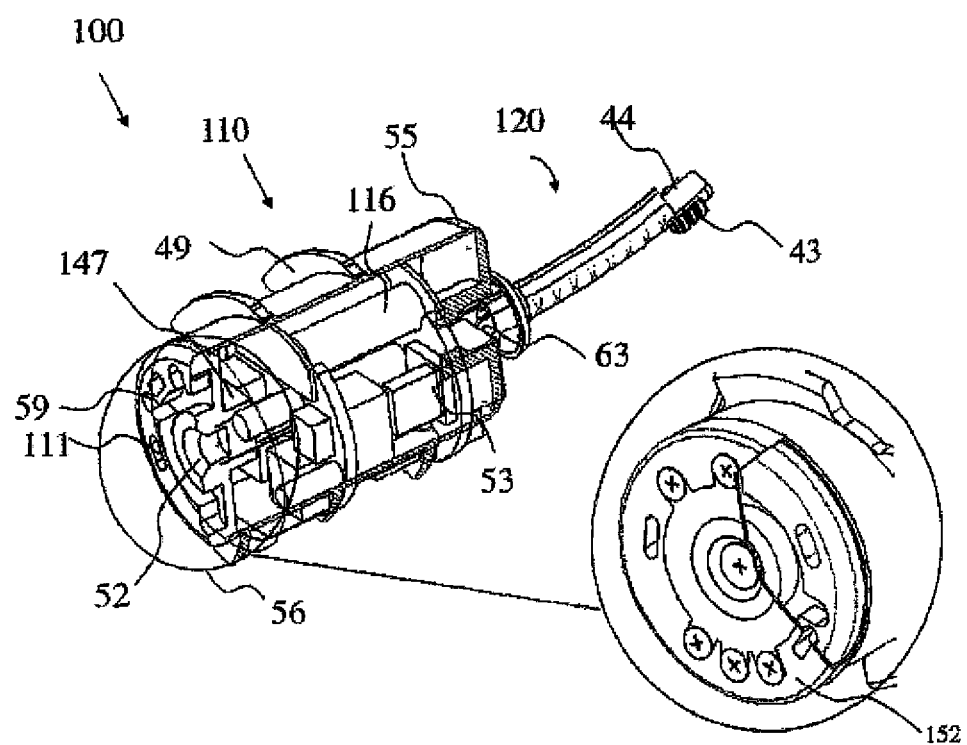
As shown in FIG. 6, the insert body comprises a shutter, that protects the uterine insert in the uterus.

As shown in FIG. 6, the insert body 110 comprises a shutter 152, which protects the uterine insert in the uterus, i.e. the electrical circuits and components described above, after deployment of the uterine insert 100, i.e. as soon as the uterine insert 100 is disconnected from the module. In some embodiments the system is configured so that the shutter automatically closes concomitantly with the uterine insert and module disengaging from each other.

Note the matching of the insert body 110 and the module insert 220, as shown in the insets of FIG. 5b and FIG. 6.
1. The monitoring system is configured to allow diagnosis of the readiness of the uterus to fertilization. Referring to FIGS. 5a and 6, the system 1000 further comprises an illumination component 123 and an imaging component 124 such as a camera. The illumination component may comprise a Light Emitting Diode (LED), an ultra violet light source, an infra red light source, incandescent light source or any combination thereof. The module body 110 comprises power supply means such as a battery 116, which provides power to the illumination component and to the imaging component, and in some embodiments to other components such as a thermometer. The optical system comprising the illumination component, the imaging component and the power supply are configured to allow the physician to properly direct the uterine insert 100. In preferred embodiments the system 1000, typically in particular the camera 124, is also configured to allow a clear view of the uterus' walls, i.e., the endometrium. In some embodiments the camera 124 is movable by remote control.

The battery also provides power to a pump 147, that will described after completing the discussion on the monitoring components.

Returning to FIG. 1, the imaging component transmits image signals to the system control device 300, which in turn transmits to a screen 400. In alternative embodiments (not shown) the control device transmits data representative of the measurement signals to a storage device, from which the data can be retrieved, manipulated and displayed on various display devices. The display may help in continuously assessing the condition of various physiological features in the uterus lining, such as gland size and blood vessel density, as well as changes in their condition over time. The screen displays images that help the physician navigate the probe 100 and to follow the condition of the uterus over an extended period of time without needing to perform repeated manual invasive procedures. In some embodiments the screen 400 is remote from the uterine insert, for example in a physician's office, so that the visual monitoring of the patient by the physician does not require the patient's presence. The imaging component may comprise a digital camera which may include CCD sensors and/or CMOS sensors, opto-mechanical parts, lenses, shutters, a PCB etc as known in the art.

In some embodiments the navigation is assisted by continuous ultrasound imaging of the uterus. In some embodiments the navigation is guided by the ultrasound imaging alone, and the system does not comprise an imaging component and illuminating component.

As shown in FIG. 4, the uterine insert further comprises sensors 125 that may comprise a matrix of bioelectrical impedance sensors/electrodes for monitoring of the uterus tissue, in order to directly inspect endometrial parameters such as bioelectrical impedances, and non-directly evaluate parameters such as vascularity, mucosa dimensions and mucosa composition. These parameters are assessed through the tissue response to electromagnetic signals of different amplitudes and frequencies. Such sensors are well known in the art [Rezac P., Theriogenology 2008; 70(1):1 1-14]. Other embodiments do not comprise such sensors, or comprise other sensors instead/in addition, such as pH sensors. Similarly to the optical component, the system is configured in these embodiments to allow signals to be transmitted from these sensors to a system control device, from where they are accessible to analysis by a physician.

The invention can be embodied in various embodiments, some of which have been described above. In some cases at least, a physician may identify during a standard ultrasound, according to the patient vaginal, cervix and uterus structure, what kind and size of the uterine insert should be installed for the patient, and optionally the working profile and programming actions needed in order to properly monitor, and optionally treat, the patient.

Figure 7:
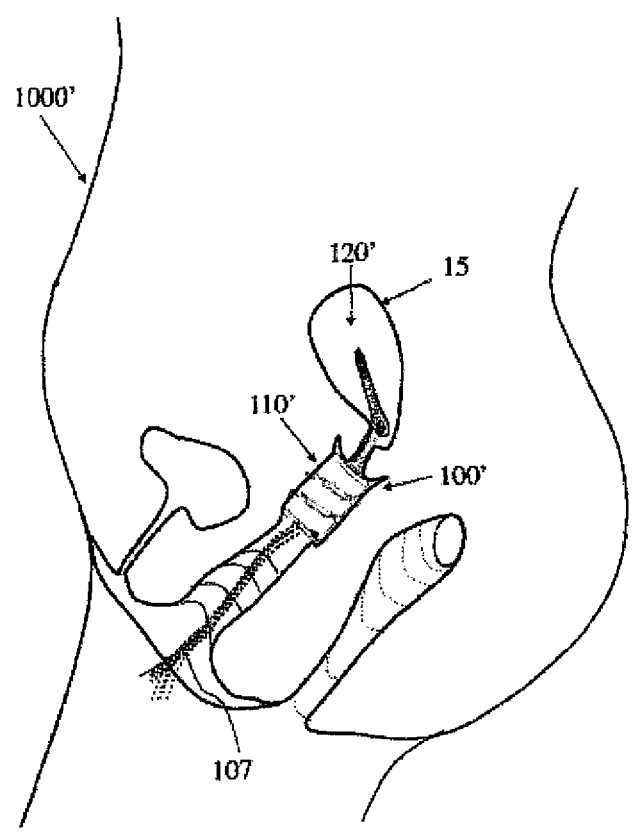
FIG. 7 schematically depicts another uterine insert embodiment, of another system.

FIG. 7 schematically depicts another uterine insert embodiment 100', of another system 1000', after disconnection from the module (not shown) and in the desired position in the uterus 15. The uterine insert 100' comprises a cord 107 that may have one or more roles: allowing wired communication between the uterine insert 100' and the system control device (not shown), such as one or more of the following outputs from the system control device to the uterine insert 100': image acquisition parameters (e.g., exposure illumination power and spectrum, illumination angle, filters engagements, polarizer engagement); electric current (for impedance measurements for example); anti-body depositions; fluorophore depositions; hormones depositions; depositions of pharmaceutical compositions, and disinfectant depositions. In addition, the system may be configured to allow the system control device to receive via the cord 107 one or more of the following inputs from the uterine insert 100': Still and/or video images; impedance signals; signals reflecting mucosa acidity; signals representing mucosa composition (e.g. hormone content and concentration); fluorescence measurement signals; and temperature measurements. The cord 107 can also be used to help pull the device 100" out for replacement, maintenance or when the monitoring is completed. Yet another role in some embodiments is to help drainage outside the vagina. In other embodiments these functions can also/instead be performed remotely and wirelessly, from a control unit that is placed on or near (and outside) the patient's body.

Figure 5C:
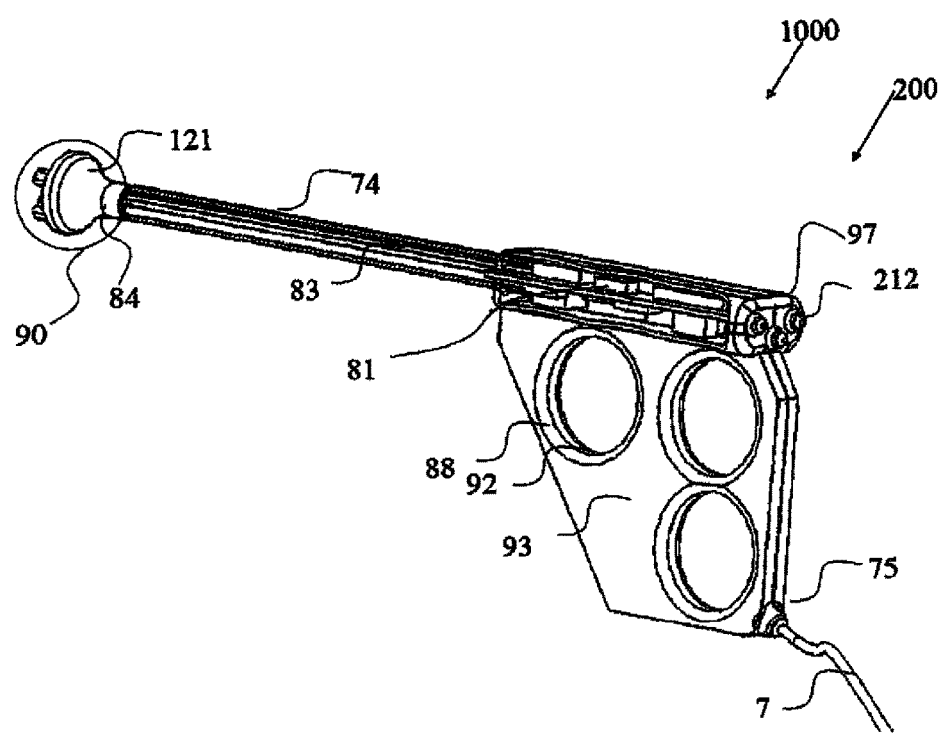
FIG. 5c shows the same module in a rear perspective sectional view.

The depositions may be performed using the help of an external pump, such as one located in the system control device, or an internal pump, such as the pump 147 in the uterine insert 100 (FIG. 5). The internal pump may also be configured to allow suction of excess fluids in some embodiments.

Figure 8:
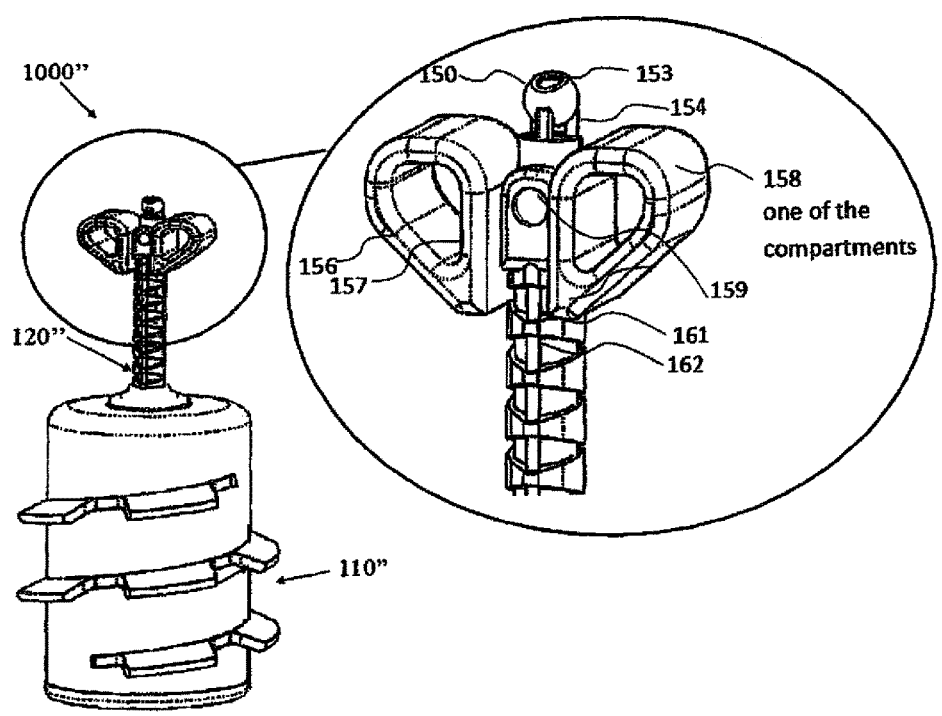
FIG. 8 illustrates in a side view a uterine insert of another system embodiment.

FIG. 8 illustrates in a side view a uterine insert 100''' of another system embodiment 1000'''. At a distal end 163 of the insert extension 120''' there are stabilizing elements 156 which function as anchor elements for the insert extension 120''' against the uterus walls, for example to allow a fixed distance from camera to the walls. Inside the stabilizing elements there are inflatable elements 157 which can be deflated and inflated from outside the uterus. Each inflatable element forms an asymmetric triangular torus with a hole that enhances attachment of the uterine insert 100''' since tissue can enter the hole and form another anchoring location. The inflatable elements 157 may be inflated with air or fluid from a "feeding tube" during the deployment procedure. Before the insert 100''' is taken out, the inflatable elements 157 are deflated and collapsed to allow easy retraction of the insert 100'''.

The inflatable elements 157 comprise compartments 158 which may allow improved control of the inflating/deflating actions. Some embodiments comprise the inflatable elements but the inflatable elements do not comprise the compartments.

Referring back to FIG. 5a, the figure shows an inflatable element 43 in collapsed state.

The distal end 163 comprises an imaging housing 159. At the distal side of the housing 159 there are legs 154 that support a nozzle 150 which comprises a spraying hole 153 through which liquid can be delivered such as solutions of hormones and/or antibodies and/or fluorophores, for example to allow detection of substances indicative of the state of the uterus in relation to readiness for fertilization. In some embodiments (not shown) the insert extension further comprises at least one washing nozzle positioned and oriented to allow washing the lens of the camera.

In preferred embodiments all of the parts of the uterine insert 100'' are coated with an anti-bacterial material.

Figure 9:
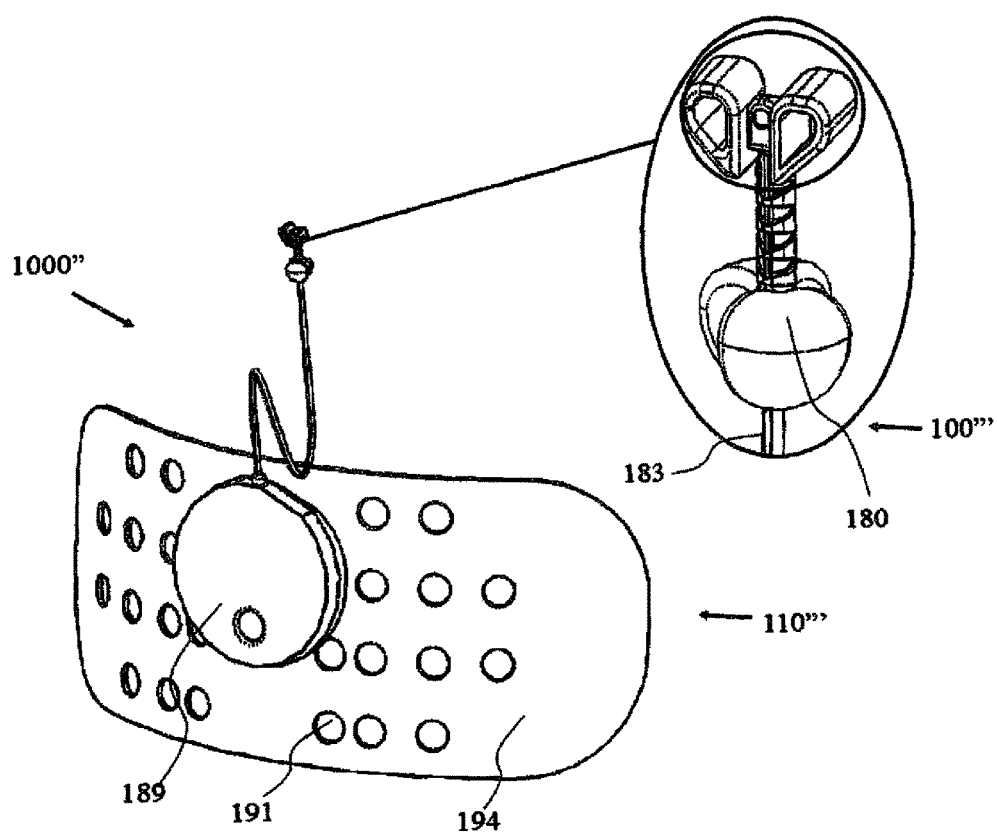
FIG. 9 shows another embodiment in a perspective view.

FIG. 9 shows another embodiment 1000''' in a perspective view. The insert body 110''' can be positioned outside the woman's vagina. The insert body 110''' comprises wings 194, with holes 191, that together allow attaching the insert body to the patient, and a housing 189 within which monitoring features and other features may be installed. The insert extension 200''' comprises an inflatable anchor 180, e.g. balloon (which may comprise several subunits) for anchoring the insert body 110''' to the vagina, housing 159 and a feed cord 183.

Figure 10:
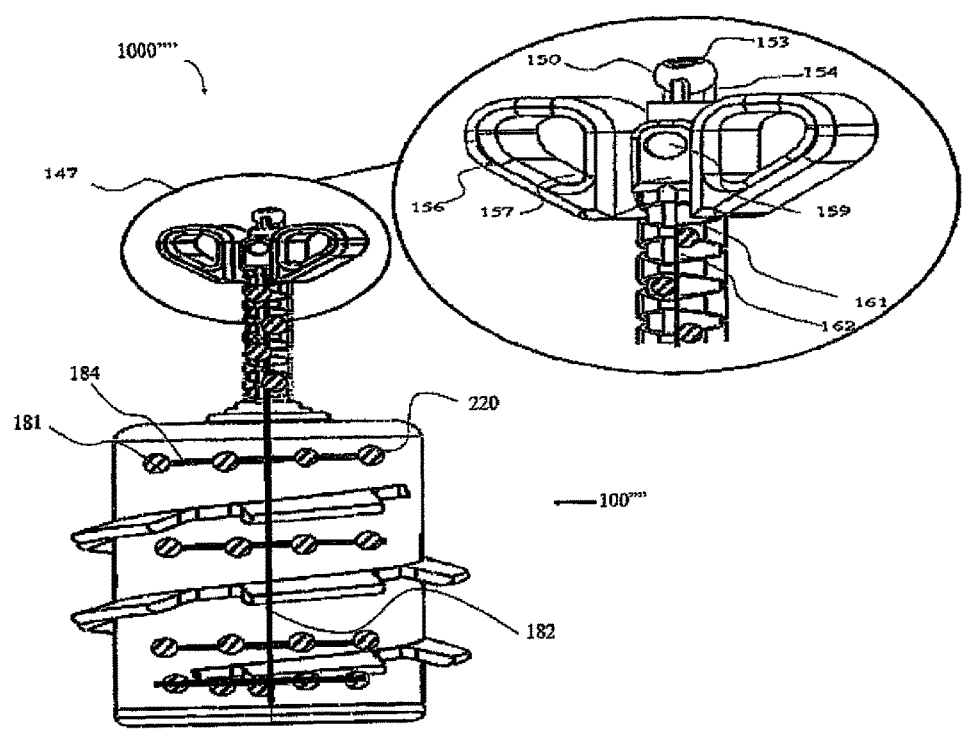
FIG. 10 depicts a uterine insert in a system similar to the uterine insert described in FIG. 8, allowing deposition of material.

FIG. 10 depicts a uterine insert 100'''' in system 1000'''', similar to the uterine insert 100' described in FIG. 8, allowing deposition of material such as disinfectant during deployment and removal of the uterine insert 1000''' and optionally during withdrawal thereof. Deposition outlet pores 181 are located on the insert body 110'''' as well as along the insert extension 120''''. A primary feeding channel 182 for depositing substances may be provided for splitting flow of the deposited material to multiple deposition secondary channels 184 to evenly cover a target area. Other channels or the same channel may also serve to provide liquid to one or more of the nozzles described above. The uterine insert 100'''' comprises as described above: nozzle 150; legs 154; inflatable elements 156 with asymmetric hole 157; a steering cable 162, and further comprises bending section vertebrae 161.

Figure 11:
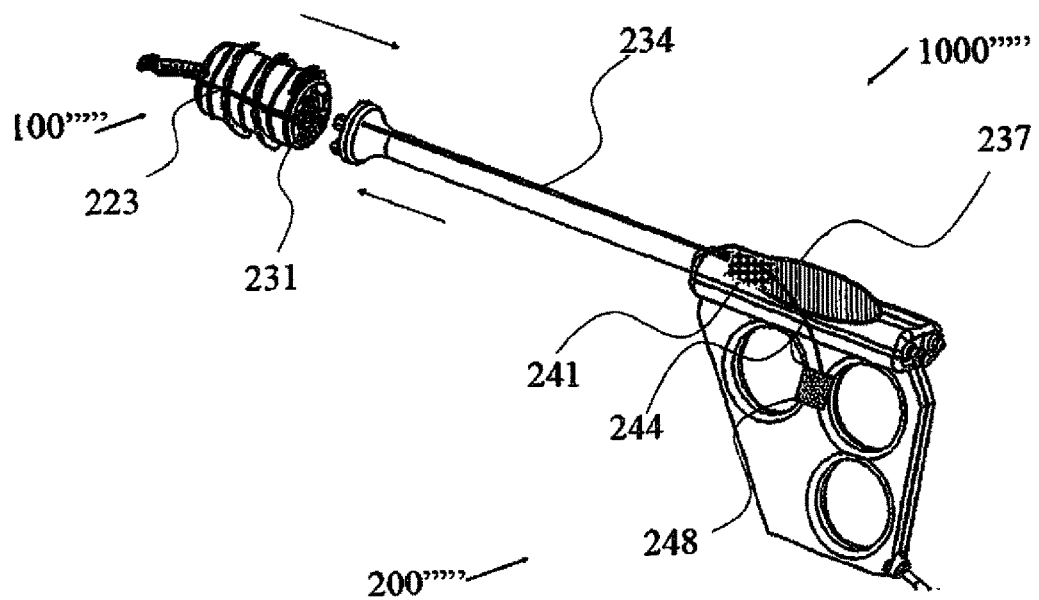
FIG. 11 schematically illustrates in perspective view the system shown in FIG. 10, now showing now as well the module.

FIG. 11 schematically illustrates in perspective view the system 1000''''', showing now as well the module 200'''''. The module 200''''' comprises: an installation tool substance feeding tube 234; a substance container 237; a substance compression unit 241; a trigger control cable 244, and a trigger 248. A connector (not shown) may connect the feeding tube 234 to the primary channel 182. Pressing the trigger leads to the cable 244 activating the compression unit 241, that releases material from the container 237 through the tube 234 and thereon out of the uterine insert 110'''''.

Figure 12:
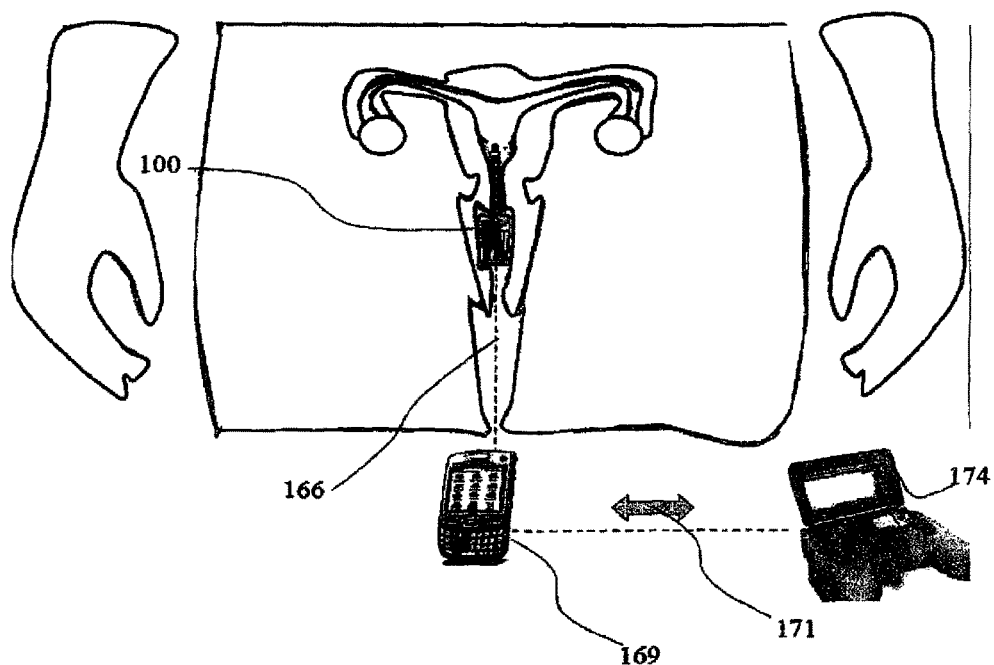
FIG. 12 schematically depicts system usage methodology during the treatment procedure, according to one aspect of the invention.

FIG. 12 schematically depicts the system usage methodology during the treatment procedure, according to one aspect of the invention. After the uterine insert 100 has been installed into the patient's body, the physician supervises the treatment procedure by dual way encrypted communication with the uterine insert via transmitter 169 which amplifies the communication 166 of the installed device and broadcasts it 171 to the physician data manager such as a computing device 174 or the like.

Figure 13:
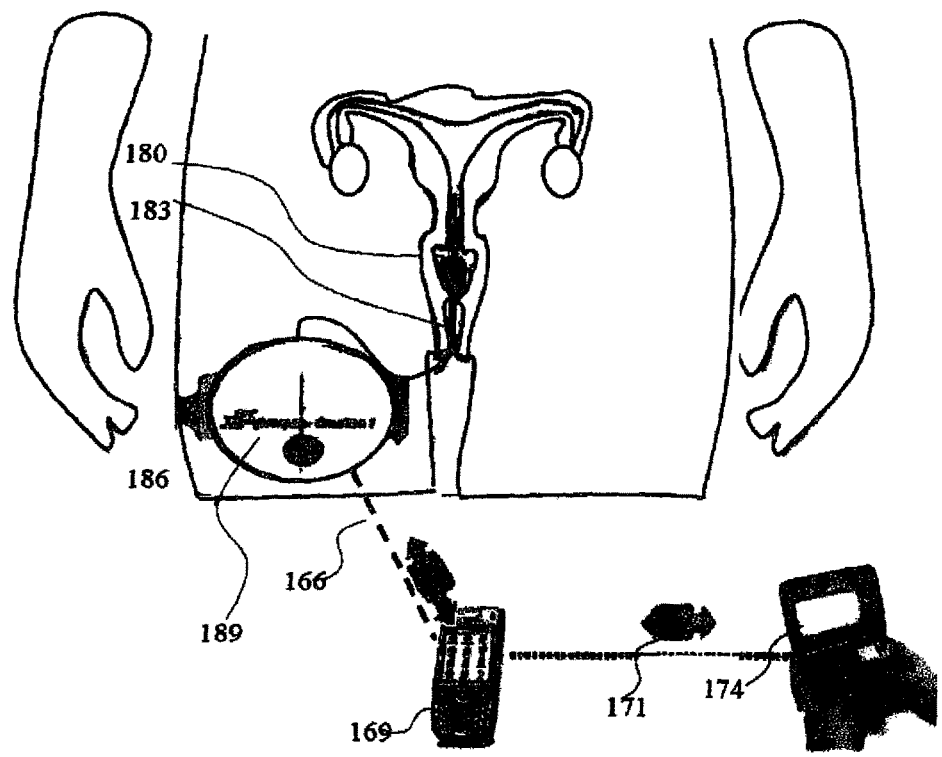
FIG. 13 schematically depicts usage methodology during the treatment procedure, in a similar embodiment.

FIG. 13 schematically depicts usage methodology during the treatment procedure, in a similar embodiment. After the uterine insert 100 has been installed into, the patient's body the physician can supervise the treatment procedure by dual way encrypted communication with the uterine insert via transmitter 169 which amplifies the communication 166 of the installed device and broadcasts it 171 to the physician data manager such as computer 174 or the like.

The present invention is related to systems and methods for patient preparation for fertilization procedures by the continuous monitoring of the uterus tissue and possibly means for substance administration (e.g., drugs, hormones, staining dyes, contrast agents, disinfectants, etc.). The device is placed in the patient's reproductive system via her natural orifice.

The system may include various sensors such as video camera integrated with a magnifying device ("mini-microscope") as well as communication means, anchoring, stabilization and fixation elements, deposition elements and/or the like.

According to one aspect, a method is provided that comprises: visual monitoring of the uterus tissue with any of the systems described above, in order to inspect endometrial parameters such as glands number and number density, size, distribution, blood vessel density, blood vessel distribution (size and spatial), blood oxygen saturation and total oxygen concentration, as well as other anatomical parameters that evolve during the uterus natural cycle and during fertilization treatments.

In some embodiments the system and method include dark-field illumination or oblique illumination and polarized illumination (bright or dark field or oblique) optionally accompanied by polarizers in front of the visual system of the uterus endometrium.

In some systems and method continuous monitoring of the endometrium acidity (pH-metry) is provided by suitable means configured to allow the monitoring.

The deposition units describe above may be used for staining dyes and fluorophores, either free or linked to biological compounds (e.g., antibodies).

Alternatively or in addition, a deposition unit may serve for the topical administration of hormones and drugs or distribution of disinfectants and sanitizers. The deposition can be actively performed during system deployment or extraction or can be continuously performed while the unit is already installed in its final position.

Various embodiments similar to the monitoring systems described above may be used or adapted to be used for veterinarian purposes, such as on mammals: horses, cows, sheep, goats, dogs, etc.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A monitoring system comprising:
a uterine insert configured to be positioned in a uterus having walls over an extended period of time and comprising an insert body comprising a socket and an insert extension,
wherein the insert body is configured to be coupled to the insert extension and the insert body and/or the insert extension comprise a flexible engagement member,
wherein the insert extension comprises at least one sensor;
a deployment module having a plug configured to removably engage the socket in the insert body,
the uterine insert being configured to undergo bending when the insert body is engaged with the deployment module allowing the insert extension to travel through a vagina and a cervix and into the uterus; and
a system control processor operationally coupled to continuously receive signals from the at least one sensor and to convert the signals into data representing the signals,
wherein the monitoring system is configured to allow monitoring of uterus tissue.

2. The system of claim 1, wherein the flexible engagement member is selected from a group consisting of curved and notched fins, inflatable elements, and combinations thereof.

3. The system of claim 2, wherein the uterine insert has a longitudinal axis, and wherein the fins point away from the insert extension and at an oblique angle relative to the axis.

4. The system of claim 2, wherein the fins are retractable.

5. The system of claim 2, wherein the inflatable elements each comprise an asymmetric hole.

6. The system of claim 1, wherein the uterine insert comprises a microscope, wherein the microscope comprises a camera.

7. The system of claim 6, further comprising an illumination component configured to illuminate for the camera.

8. The system of claim 1, wherein the uterine insert further comprises a shutter configured to shut when the uterine insert is disengaged with the module.

9. The system of claim 1, wherein the uterine insert further comprises a power supply unit electrically coupled to the at least one sensor.

10. The system of claim 1, wherein the uterine insert comprises at least one anti-bacterial composition capable of preventing ascending contamination.

11. The system of claim 1, wherein the insert extension further comprises at least one drawstring that is coupleable to the module, such that when the module is engaged with the uterine insert, the module can be employed to draw the at least one drawstring and thereby bend the insert extension.

12. The system of claim 1, configured to allow deposition of substances from the insert extension through deposition pores along the insert extension and/or a nozzle at a tip of the insert extension.

13. The system of claim 12, wherein the insert extension comprises a primary feeding channel leading throughout the insert extension and to the pores and/or to the nozzle.

14. The system of claim 12, further comprising a power supply unit electrically coupled to a pump, wherein the pump is coupled to the primary feeding channel.

15. The system of claim 1, wherein the at least one sensor is a camera and the system further comprises at least one nozzle configured to allow washing at least one lens of the camera.

16. The system of claim 1, wherein the at least one sensor is a camera and the camera is movable by remote control.

17. The system of claim 1, wherein the at least one sensor is a camera and the camera is configured to allow a clear view of the walls of the uterus.

18. The system of claim 1, wherein the insert extension further comprises a cord, configured to allow performing at least one of the following actions:
wired communication between the uterine insert and the system control device;
to help withdraw the insert extension; and
to help drainage outside the vagina wherein the insert extension is installed.

19. The system of claim 1, comprising a display operationally coupled to display the data from the system control device.

20. The system of claim 1, wherein the monitoring system monitors at least one characteristic selected from a group consisting of glands number, glands number density, glands size and glands size distribution, blood vessel density, blood vessel distribution, blood oxygen saturation, and total oxygen concentration.

21. The system of claim 1, wherein the sensor is selected from a group consisting of a camera, a thermometer, a pH sensitive electrode, a bioelectrical impedance sensor, and combinations thereof.

22. The system of claim 1, wherein at least one of an output selected from a group consisting of image acquisition parameters, electric current, anti-body depositions, fluorophore depositions, hormones depositions, depositions of pharmaceutical compositions, and disinfectant depositions are transferable from the system control device to the uterine insert, and at least one of an input selected from a group consisting of still and/or video images, impedance signals, signals reflecting mucosa acidity, signals representing mucosa composition, fluorescence measurement signals, and temperature measurements are transferrable from the uterine insert to the system control device.

23. The system of claim 22, wherein the transfer of data from at least one output and at least one input is wireless.

* * * * *